US011938318B2

(12) United States Patent
Forsell

(10) Patent No.: US 11,938,318 B2
(45) Date of Patent: Mar. 26, 2024

(54) APPARATUS FOR TEMPORARY MALE CONTRACEPTION

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/123,330

(22) PCT Filed: Oct. 9, 2009

(86) PCT No.: PCT/SE2009/051130
§ 371 (c)(1),
(2), (4) Date: Apr. 8, 2011

(87) PCT Pub. No.: WO2010/047644
PCT Pub. Date: Apr. 29, 2010

(65) Prior Publication Data
US 2011/0192402 A1 Aug. 11, 2011

Related U.S. Application Data

(60) Provisional application No. 61/227,810, filed on Jul. 23, 2009.

(30) Foreign Application Priority Data

Oct. 10, 2008 (SE) .................... 0802137-0

(51) Int. Cl.
*A61F 6/00* (2006.01)
*A61F 6/02* (2006.01)
(Continued)

(52) U.S. Cl.
CPC ............ *A61N 1/36007* (2013.01); *A61F 6/02* (2013.01); *A61F 6/206* (2013.01); *A61F 5/0059* (2013.01);
(Continued)

(58) Field of Classification Search
CPC .... A61F 6/00; A61F 6/02; A61F 6/202; A61F 6/204; A61F 6/206; A61F 2/0036; A61F 6/20–24; A61B 17/12; A61B 17/1204
(Continued)

(56) References Cited

U.S. PATENT DOCUMENTS 3,699,957 A * 10/1972 Robinson .................. A61F 6/24
128/843
3,749,098 A * 7/1973 De Bennetot ................... 600/30
(Continued)

FOREIGN PATENT DOCUMENTS

DE 199 09 427 5/2000
JP 3123543 A2 5/1991
(Continued)

OTHER PUBLICATIONS

International Search Report for PCT/SE2009/051130, dated Jan. 8, 2010.
(Continued)

*Primary Examiner* — Adam Baker

(57) ABSTRACT

The present invention relates to a male contraception apparatus for obtaining temporary sterility of a male mammalian individual. The apparatus has an implantable restriction device adapted to restrict vas deference in the region downstream the ampulla during a controlled period in order to preventing sperms to reach the urethra. Further, the apparatus has a control device for controlling the operation of the restriction device.

24 Claims, 14 Drawing Sheets

(51) Int. Cl.
*A61F 6/20* (2006.01)
*A61N 1/36* (2006.01)
A61F 5/00 (2006.01)
A61N 1/05 (2006.01)
A61N 1/378 (2006.01)

(52) U.S. Cl.
CPC ..... *A61F 2250/0001* (2013.01); *A61N 1/0551* (2013.01); *A61N 1/3787* (2013.01)

(58) Field of Classification Search
USPC ................ 128/842, 843, 887; 600/29, 30
See application file for complete search history.

(56) References Cited

U.S. PATENT DOCUMENTS

| | | | |
|---|---|---|---|
| 3,750,194 A * | 8/1973 | Summers ............... | A61F 2/004 623/23.66 |
| 3,817,237 A | 6/1974 | Bolduc | |
| 4,256,094 A * | 3/1981 | Kapp ................... | A61B 5/022 600/488 |
| 4,587,954 A * | 5/1986 | Haber ................... | A61F 2/004 128/DIG. 25 |
| 4,958,630 A * | 9/1990 | Rosenbluth ........... | A61B 17/12 600/40 |
| 6,067,991 A * | 5/2000 | Forsell ................. | A61F 5/0053 128/899 |
| 6,162,238 A * | 12/2000 | Kaplan ................. | A61F 2/0036 604/9 |
| 2003/0032857 A1* | 2/2003 | Forsell ................. | A61F 2/0036 600/30 |
| 2003/0105385 A1* | 6/2003 | Forsell ................. | 600/29 |
| 2003/0125605 A1* | 7/2003 | Forsell ................. | A61F 2/26 600/40 |
| 2004/0116773 A1* | 6/2004 | Furness et al. ........ | 600/30 |
| 2005/0256364 A1* | 11/2005 | Burton et al. .......... | 600/30 |
| 2006/0047180 A1 | 3/2006 | Hedge et al. | |
| 2007/0073099 A1* | 3/2007 | Forsell ................. | 600/31 |
| 2008/0195172 A1* | 8/2008 | Furness ............... | A61F 2/0036 607/41 |
| 2009/0131959 A1* | 5/2009 | Rolland ............... | A61F 2/04 606/158 |

FOREIGN PATENT DOCUMENTS

| | | |
|---|---|---|
| WO | 1999063907 A1 | 12/1999 |
| WO | WO 0154615 | 8/2001 |
| WO | WO 2007/124128 | 11/2007 |
| WO | WO 2009/048389 | 4/2009 |

OTHER PUBLICATIONS

Written Opinion of the International Searching Authority for PCT/SE2009/051130, dated Jan. 8, 2010.
S. K. Guha, A. Mateen Ahmed and H. Kaur: "Feasibility study of the reversible occlusion device for the vas deferens", Medical and Biological Engineering and Computing, vol. 14, No. 1, Jan. 1976 (Jan. 1976), pp. 15-18, XP009156846, ISSN: 0140-0118.
Extended European Search Report in Application No. 09822269.8-2305, completed Feb. 24, 2012.

* cited by examiner

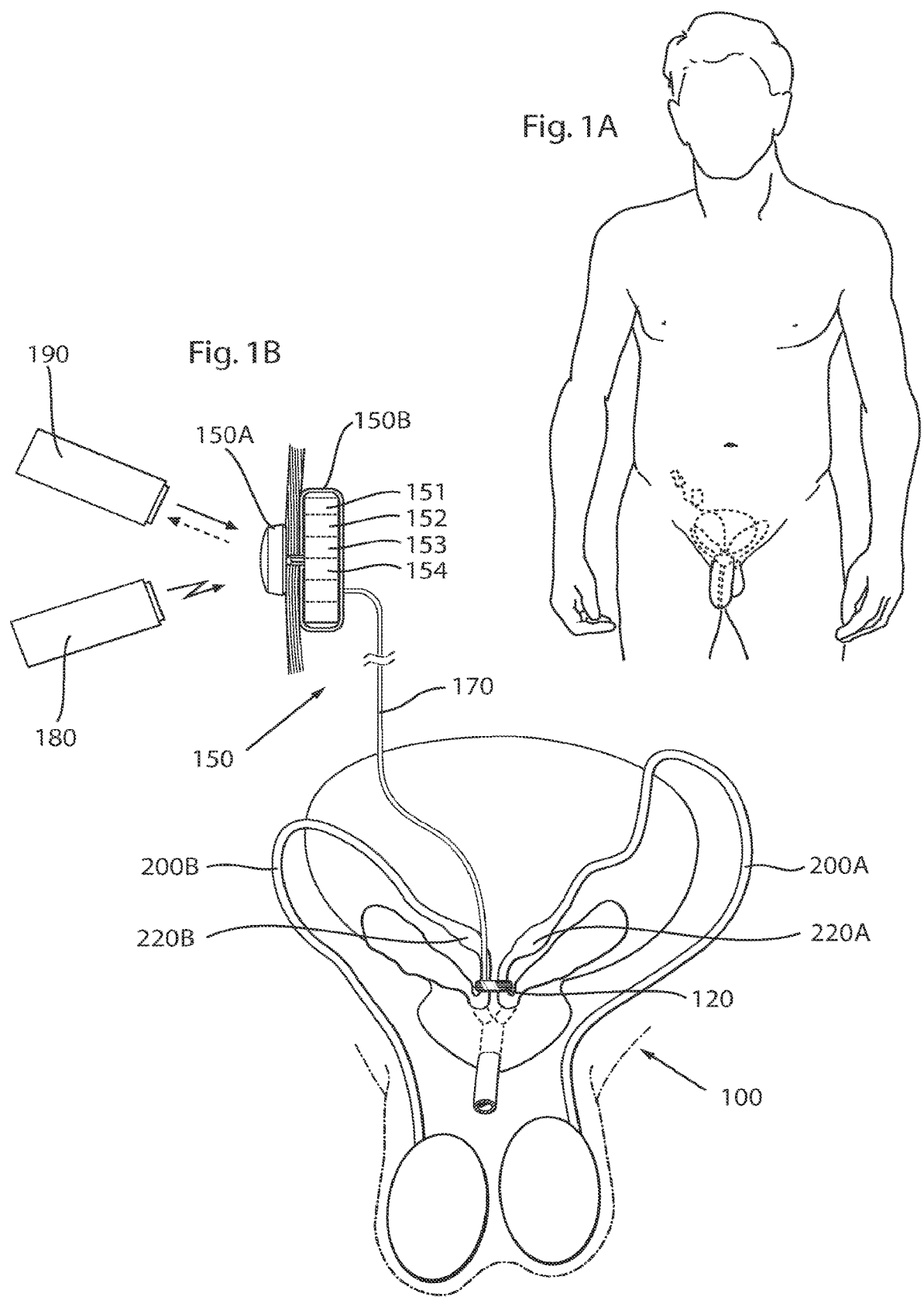

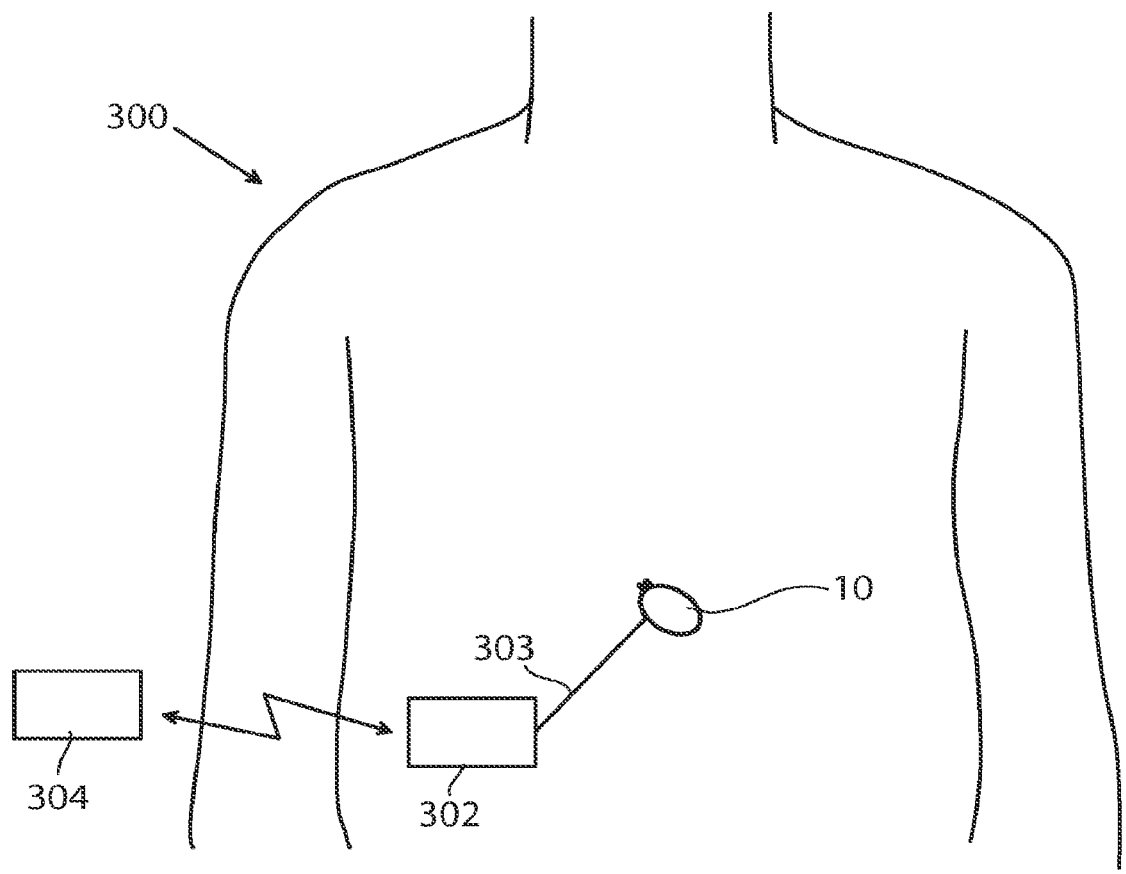

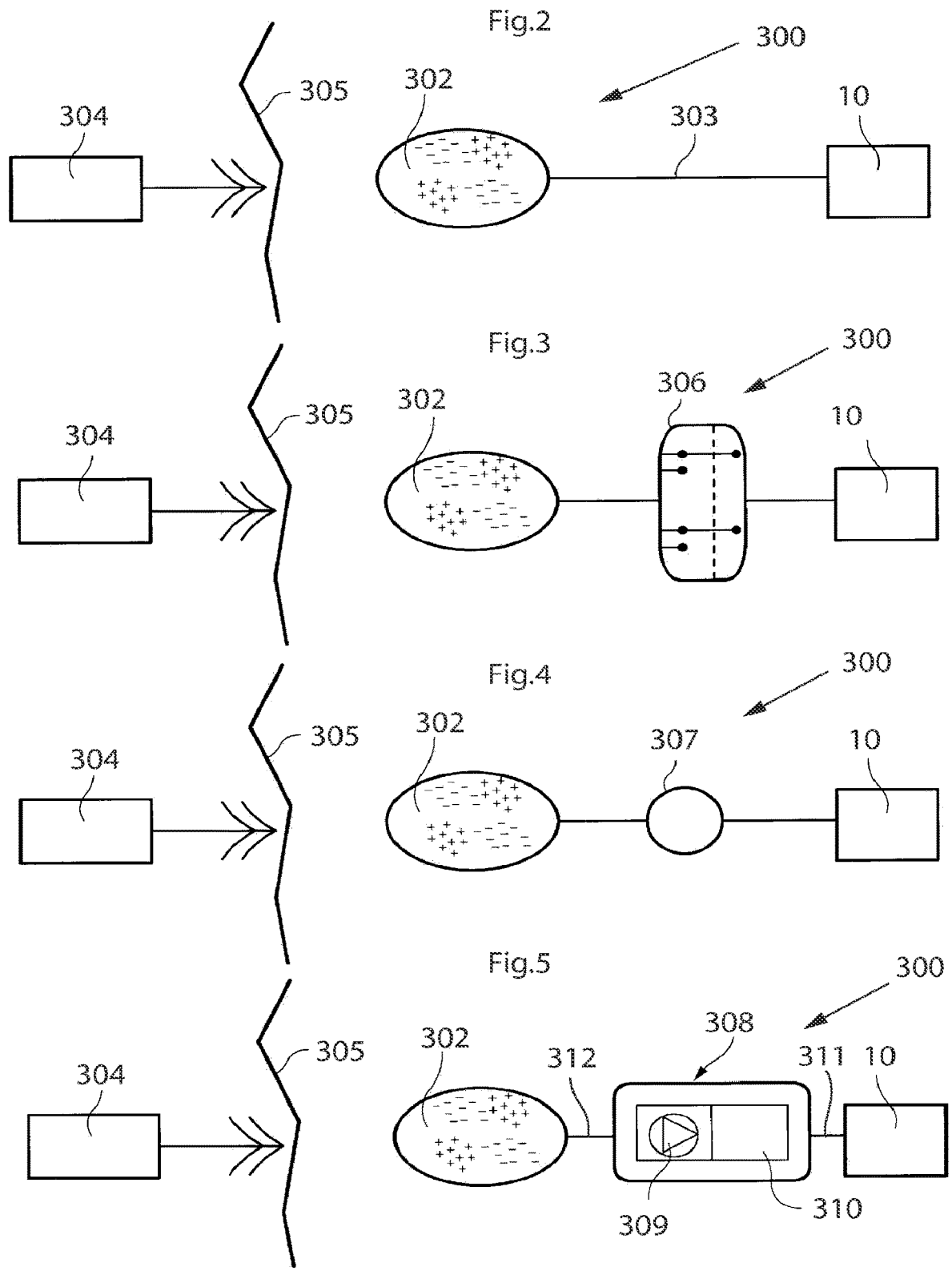

APPARATUS FOR TEMPORARY MALE CONTRACEPTION

This application is the U.S. national phase of International Application No. PCT/SE2009/051130, filed 9 Oct. 2009, which designated the U.S. and claims the benefit of U.S. Provisional No. 61/227,810 filed 23 Jul. 2009 and claims priority to Swedish Patent No. 0802137-0 filed 10 Oct. 2008, the entire contents of each of which are hereby incorporated by reference.

FIELD OF INVENTION

The present invention relates generally to a system and an apparatus for male contraception that operates to close a vas deferens during a controlled temporary period.

BACKGROUND

A common route of male contraception is occlusion of vas deferens (the sperm transporting duct). Vasectomy is a surgical intervention to cut vas deferens and is most frequently a confinement to permanent sterility. More recently, other alternatives have become available by the provision of devices to be inserted into vas deferens and obtain a sealing effect. One such technique is described in U.S. Pat. No. 6,513,528 that relates to a set of silicone plugs for insertion into vas deferens. However, even if this technology represents a possibility to reverse the individual to fertility is also associated with side effects, such as sperm antibody formation. It is therefore a need for a more gentle technique to obtain controlled male contraception which admits reversibility with minimal affection of body functions. The object of the present invention as it is outlined below is an apparatus, a system and a methodology that provides more safety and convenience with male contraception based on occlusion of vas deferens.

DESCRIPTION OF THE INVENTION

In general terms, the present invention relates to a male contraception apparatus for obtaining temporary sterility of a male mammalian individual. The apparatus comprises an implantable restriction device adapted to restrict vas deferens in the region downstream of the ampulla during a controlled period, said device thereby being capable of preventing sperms to reach the urethra. The apparatus further comprises a control device for controlling the operation of the restriction device. The restriction device may comprise a hydraulic or mechanical constriction device as well as a stimulation device for, independently or together in any combination, temporarily restrict vas deferens.

In this context restriction of vas deferens means that this lumen is occluded in a manner to prevent sperms to reach the urethra by operating on vas deferens from the outside. The terms "vas deferens" may include one vas deferens or both vasa deferentia. When explaining the controlled restriction of vas deferens according to the invention also other terms like "lumen" or "tissue portion" or "body organ" are used, but such terms shall be regarded as functional synonyms. The term "ampulla" refers to the enlargement of vas deferens close to where it meets the seminal vesicle.

The term "downstream the ampulla" refers to a location after the ampulla in the direction of the urethra and the seminal vesicle. Consequently, "upstream the ampulla" would refer to a location on the vas deferens before the ampulla in the direction towards the testicle. That the restriction device is adapted to restrict vas deferens in this specific region preferably means that it is designed to be accommodated in this region of the body.

By accomplishing a restriction of vas deferens downstream of the ampulla, the presently invented apparatus admits a reliable temporary sterilization by shielding of sperms compartmentalized in the ampulla, whereby the apparatus immediately may exert its contraceptive effect. Even if the principal utility of the apparatus is to prevent sperm transport for a controlled, temporary period, for example during sexual intercourse by activating the restriction device, certain embodiments of the invention also admits support of transporting sperms through vas deferens to assist individuals having impairments in this transportation system. Advantageously, the present invention admits a very limited time period the restriction needs to be restricted. Existing treatments need to be closed at least 5 days before it is safe, the life time of a sperm, thus risking damaging vas deferens. Furthermore, the apparatus prevents from that sperms accumulate in the vas deferens due to long term restriction which may lead to undesired complications.

The restriction device is very carefully be adapted to the specific position downstream the ampulla. The amount of space is limited and the requirements are specific to allow placement in this region between the prostate and the ampulla of vas deferens. Because the ampulla comprises a reservoir of sperm the restriction is performed in the downstream region to prevent any possibility to sperm reaching the urethra during intercourse. The restriction device according to invention can also when relevant be adapted to accomplish restriction of closely located outlet duct of seminal vesicles. A simultaneous restriction of this outlet duct should be regarded as one of the effects obtainable with the present invention.

According to one embodiment of the invention, restriction device comprises a constriction device for constricting at least one portion of a tissue wall of vas deferens downstream the ampulla to stop the flow in the vas deferens. For this purpose, the apparatus comprises an adjustable restriction device and an operation device for mechanically or hydraulically operating the adjustable restriction device to change the restriction of a wall portion of vas deferens. The operation device preferably operates the restriction device in a non-magnetic and/or non-manual manner. Preferably, the operation device comprises an electrically powered operation device, such as motor or a servo system. The term "servo system" means that the system includes a mechanism that transfers a weak force acting on a moving element having a long stroke into a strong force acting on another moving element having a short stroke. According to one alternative the restriction device comprises a constriction device comprising at least two elongated clamping elements extending along the organ in the direction of flow in the patient's vas deferens on different sides of the organ, and the operation device operates the clamping elements to clamp the wall portion between the clamping elements to constrict the wall portion. The operation device can alternatively comprise hydraulic means for hydraulically adjusting the restriction device and a reverse servo operatively connected to the hydraulic means. The term "reverse servo" is to be understood as a mechanism that transfers a strong force acting on a moving element having a short stroke into a weak force acting on a moving element with a long stroke. Preferably, the reverse servo comprises at least two implantable reservoirs comprising hydraulic fluid, and preferably a first reservoir is a subcutaneously implantable regulation reservoir. The reverse servo further comprises a second implantable servo reservoir which preferably is in fluid connection with the regulation reservoir. In one embodiment the second servo reservoir directly controls the expansion/contraction of the constriction device. In another embodiment, the servo reservoir indirectly controls the expansion/contraction of the constriction device, wherein the reverse servo further comprising a third reservoir adapted to be implanted in the abdomen or retroperitoneum or pelvic region and being operatively connected to the second servo reservoir for displacing hydraulic fluid of said third reservoir to operate the constriction device. Suitably, the third reservoir has a larger volume than the first reservoir. The third reservoir can be in fluid connection with the constriction device and the servo reservoir can control the third reservoir with a mechanical interconnection Alternatively, the restriction device comprises a non-inflatable mechanical constriction device and the operation device comprises hydraulic means that hydraulically adjusts the mechanical constriction device.

According to another embodiment of the invention, the restriction device comprises a stimulation device for stimulating a wall portion of the tissue wall of vas deferens in the region downstream the ampulla to contract said wall portion to influence the flow in vas deferens. A control device controls the stimulation device to stimulate the wall portion and the control device is preferably operable from outside the patient's body to control an implantable source of energy to release energy for use in connection with the stimulation. The stimulation device is adapted to stimulate different areas of the wall portion and the control device controls the stimulation device to intermittently and individually stimulate the areas of the wall portion. This intermittent and individual stimulation of different areas of the wall portion of the organ allows tissue of the wall portion to maintain substantially normal blood circulation during the operation of the apparatus of the invention. Various alternatives of accomplishing restriction by stimulation and useful components are described below.

It is also an embodiment of the invention that restriction device comprises a mechanically or hydraulically operated constriction as described above and a stimulation device as described above. The control device is adapted to control the constriction device and the stimulation device to in combination restrict vas deferens.

The invention also embodies a method of stimulating the ampulla comprising employing an apparatus as described having a stimulation device for restricting vas deferens downstream the ampulla. A counterflow stimulation of the ampulla is thereby obtainable.

Further the invention comprises a system including any apparatus described in previous sections. In a preferred embodiment, the system comprises at least one switch implantable in the patient for manually and non-invasively controlling the apparatus. In another preferred embodiment, the system comprises a wireless remote control for non-invasively controlling the apparatus. In a preferred embodiment, the system comprises a hydraulic operation device for operating the apparatus. In another embodiment, the system comprises comprising a motor or a pump for operating the apparatus. Other components of the system are described in more detail in the detailed part of the present description.

Stimulation

When stimulating neural or muscular tissue there is a risk of injuring or deteriorating the tissue over time, if the stimulation is not properly performed. The apparatus of the present invention is designed to reduce or even eliminate that risk. Thus, in accordance with the present invention, the control device controls the stimulation device to intermittently stimulate different areas of the wall portion of the organ, such that at least two of the areas are stimulated at different points of time that is, the stimulation is shifted from one area to another area over time. In addition, the control device controls the stimulation device, such that an area of the different areas that currently is not stimulated has time to restore substantially normal blood circulation before the stimulation device stimulates the area again. Furthermore, the control device controls the stimulation device to stimulate each area during successive time periods, wherein each time period is short enough to maintain satisfactory blood circulation in the area until the lapse of the time period. This gives the advantage that the apparatus of the present invention enables continuous stimulation of the wall portion of the organ to achieve the desired flow control, while essentially maintaining over time the natural physical properties of the organ without risking injuring the organ.

Also, by physically changing the places of stimulation on the organ over time as described above it is possible to create an advantageous changing stimulation pattern on the organ, in order to achieve a desired flow control.

The control device may control the stimulation device to stimulate one or more of the areas of the wall portion at a time, for example by sequentially stimulating the different areas. Furthermore, the control device may control the stimulation device to cyclically propagate the stimulation of the areas along the wall portion, preferably in accordance with a determined stimulation pattern. To achieve the desired reaction of the tissue wall during the stimulation thereof, the control device may control the stimulation device to, preferably cyclically, vary the intensity of the stimulation of the wall portion.

In a preferred embodiment of the invention, the control device controls the stimulation device to intermittently stimulate the areas of the wall portion with pulses that preferably form pulse trains. At least a first area and a second area of the areas of the wall portion may be repeatedly stimulated with a first pulse train and a second pulse train, respectively, such that the first and second pulse trains over time are shifted relative to each other. For example, the first area may be stimulated with the first pulse train, while the second area is not stimulated with said second pulse train, and vice versa. Alternatively, the first and second pulse trains may be shifted relative to each other, such that the first and second pulse trains at least partially overlap each other.

The pulse trains can be configured in many different ways. Thus, the control device may control the stimulation device to vary the amplitudes of the pulses of the pulse trains, the duty cycle of the individual pulses of each pulse train, the width of each pulse of the pulse trains, the length of each pulse train, the repetition frequency of the pulses of the pulse trains, the repetition frequency of the pulse trains, the number of pulses of each pulse train, and/or the off time periods between the pulse trains. Several pulse trains of different configurations may be employed to achieve the desired effect.

In case the control device controls the stimulation device to vary the off time periods between pulse trains that stimulate the respective area of the wall portion, it is also possible to control each off time period between pulse trains to last long enough to restore substantially normal blood circulation in the area when the latter is not stimulated during the off time periods.

Electric Stimulation

In accordance with a preferred embodiment of the invention, the stimulation device is an electrically powered stimulation device that electrically stimulates the tissue wall portion of the patient's bodily organ, preferably with electric pulses. This embodiment is particularly suited for applications in which the wall portion includes muscle fibers that react to electrical stimula. In this embodiment, the control device controls the stimulation device to stimulate the wall portion with electric pulses preferably in the form of electric pulse trains, when the wall portion is in the constricted state, to cause contraction of the wall portion. Of course, the configuration of the electric pulse trains may be similar to the above described pulse trains and the control device may control the stimulation device to electrically stimulate the different areas of the wall of the organ in the same manner as described above.

The electric stimulation device suitably comprises at least one, preferably a plurality of electrical elements, such as electrodes, for engaging and stimulating the wall portion with electric pulses. Optionally, the electrical elements may be placed in a fixed orientation relative to one another. The control device controls the electric stimulation device to electrically energize the electrical elements, one at a time, or groups of electrical elements at a time. Preferably, the control device controls the electric stimulation device to cyclically energize each element with electric pulses. Optionally, the control device may control the stimulation device to energize the electrical elements, such that the electrical elements are energized one at a time in sequence, or such that a number or groups of the electrical elements are energized at the same time. Also, groups of electrical elements may be sequentially energized, either randomly or in accordance with a predetermined pattern.

The electrical elements may form any pattern of electrical elements. Preferably, the electrical elements form an elongate pattern of electrical elements, wherein the electrical elements are applicable on the patient's wall of the organ, such that the elongate pattern of electrical elements extends lengthwise along the wall of the organ, and the elements abut the respective areas of the wall portion. The elongate pattern of electrical elements may include one or more rows of electrical elements extending lengthwise along the wall of the organ. Each row of electrical elements may form a straight, helical or zig-zag path of electrical elements, or any form of path. The control device may control the stimulation device to successively energize the electrical elements longitudinally along the elongate pattern of electrical elements in a direction opposite to, or in the same direction as that of, the flow in the patient's lumen.

Optionally, the control device may control the stimulation device to successively energize the electrical elements from a position substantially at the center of the constricted wall portion towards both ends of the elongate pattern of electrical elements. Where the lumen of the organ is to be kept closed for a relatively long time, the control device may control the stimulation device to energize the electrical elements, such that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the organ and without moving fluid or gas in any direction in the lumen of the organ.

The control device suitably controls the stimulation device to energize the electrical elements, such that the electrical elements currently energized form at least one group of adjacent energized electrical elements. In accordance with a first alternative, the elements in the group of energized electrical elements form one path of energized electrical elements.

The path of energized electrical elements may extend at least in part around the patient's organ. In a second alternative, the elements of the group of energized electrical elements may form two paths of energized electrical elements extending on mutual sides of the patient's organ, preferably substantially transverse to the flow direction in the lumen of the organ. In a third alternative, the elements of the group of energized electrical elements may form more than two paths of energized electrical elements extending on different sides of the patient's organ, preferably substantially transverse to the flow direction in the patient's lumen.

In accordance with a preferred embodiment of the invention, the electrical elements form a plurality of groups of elements, wherein the groups form a series of groups extending along the patient's organ in the flow direction in the patient's lumen. The electrical elements of each group of electrical elements may form a path of elements extending at least in part around the patient's organ. In a first alternative, the electrical elements of each group of electrical elements may form more than two paths of elements extending on different sides of the patient's organ, preferably substantially transverse to the flow direction in the patient's lumen. The control device may control the stimulation device to energize the groups of electrical elements in the series of groups in random, or in accordance with a predetermined pattern. Alternatively, the control device may control the stimulation device to successively energize the groups of electrical elements in the series of groups in a direction opposite to, or in the same direction as that of, the flow in the patient's lumen, or in both said directions starting from a position substantially at the center of the constricted wall portion. For example, groups of energized electrical elements may form advancing waves of energized electrical elements, as described above; that is, the control device may control the stimulation device to energize the groups of electrical elements, such that energized electrical elements form two waves of energized electrical elements that simultaneously advance from the center of the constricted wall portion in two opposite directions towards both ends of the elongate pattern of electrical elements.

A structure may be provided for holding the electrical elements in a fixed orientation. Although the structure may be separate from the constriction device, it is preferable that the structure is integrated in the constriction device, which is a practical design and facilitates implantation of the constriction and stimulation devices. Where the electrical elements form an elongate pattern of electrical elements, the structure may be applicable on the patient's organ such that the elongate pattern of electrical elements extends along the organ in the same direction as that of the flow in the patient's lumen and the elements abut the respective areas of the wall portion of the organ.

Thermal Stimulation

In another embodiment of the invention, the stimulation device thermally stimulates the wall portion of the organ. Thus, the control device may control the stimulation device to cool the wall portion, when the wall portion is constricted, to cause contraction of the wall portion. For example, the constriction device may constrict the wall portion to at least restrict the flow in the lumen, and the control device may control the stimulation device to cool the constricted wall portion to cause contraction thereof, such that the flow in the lumen is at least further restricted, or further restricted but not stopped, or stopped. Alternatively, the control device may control the stimulation device to heat the wall portion, when the wall portion is constricted and contracted, to cause expansion of the wall portion. Where the wall portion includes a blood vessel, the control device may control the stimulation device to cool the blood vessel to cause contraction thereof, or heat the blood vessel to cause expansion thereof. Where applicable, thermal stimulation may be practised in any of the embodiments of the present invention, and the thermal stimulation may be controlled in response to various sensors, for example strain, motion or pressure sensors.

Sensor Controlled Constriction and/or Stimulation Device

As mentioned above, the apparatus may comprise at least one implantable sensor, wherein the control device controls the constriction device and/or the stimulation device in response to signals from the sensor. Generally, the sensor directly or indirectly senses at least one physical parameter of the patient, or at least one functional parameter of the apparatus, or at least one functional parameter of a medical implant in the patient.

Many different kinds of sensor for sensing physical parameters may be used. For example motion sensors for sensing organ motion, i.e. natural contractions, such as stomach or intestinal contractions, pressure sensors for sensing pressure in the organ, strain sensors for sensing strain of the organ, flow sensors for sensing fluid flow in the lumen of the organ, spectro-photometrical sensors, Ph-sensors for sensing acidity or alkalinity of the fluid in the lumen of the organ, oxygen-sensors sensors for sensing the oxygen content of the fluid in the lumen of the organ, or sensors for sensing the distribution of the stimulation on the stimulated organ. Any conceivable sensors for sensing any other kind of useful physical parameter may be used.

Many different kinds of sensors that sense functional parameters of the apparatus may also be used for the control of the constriction device and/or the stimulation device. For example sensors for sensing electric parameters of implanted electric components of the apparatus, or sensors for sensing the performance of implanted motors of the apparatus.

The sensor may comprise a pressure sensor for sensing as the physical parameter a pressure in the patient's body that relates to the pressure in the lumen of the patient's bodily organ, wherein the control device controls the constriction device and/or stimulation device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the lumen during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which are settable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

BRIEF DESCRIPTION OF THE DRAWINGS

The present invention will now be described in more detail by way of non-limiting examples and with reference to the accompanying drawings, in which:

FIGS. 1A to 1F schematically an apparatus according to the invention implanted in a human.

FIG. 1G illustrates a system for treating a disease, wherein the system includes an apparatus of any of FIG. 1A to 1F implanted in a patient.

FIGS. 2-16 schematically show various embodiments of the system for wirelessly powering the apparatus shown in FIGS. 1A-1F.

DETAILED DESCRIPTION OF PREFERRED EMBODIMENTS

Figure 1C:
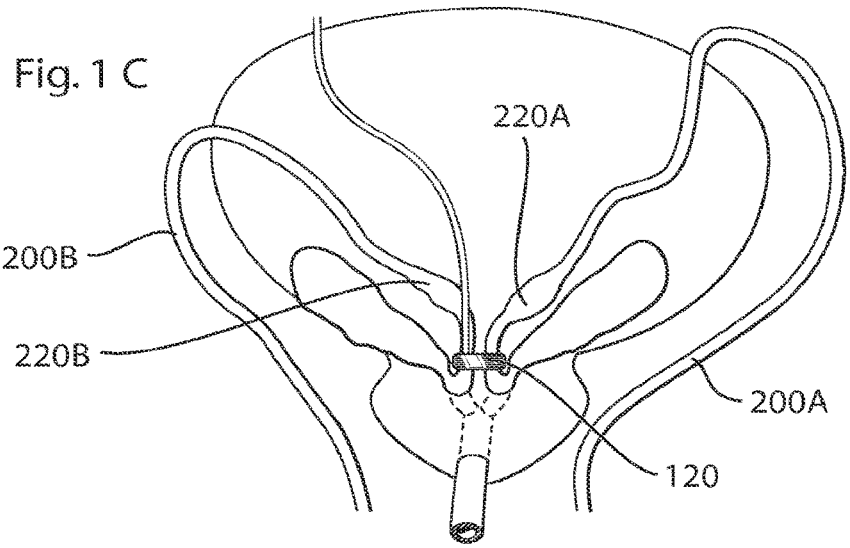
Figure 1D:
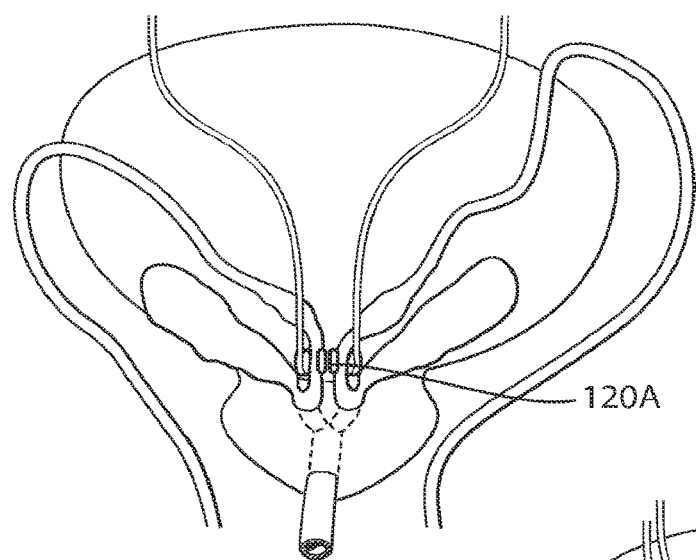
Figure 1E:
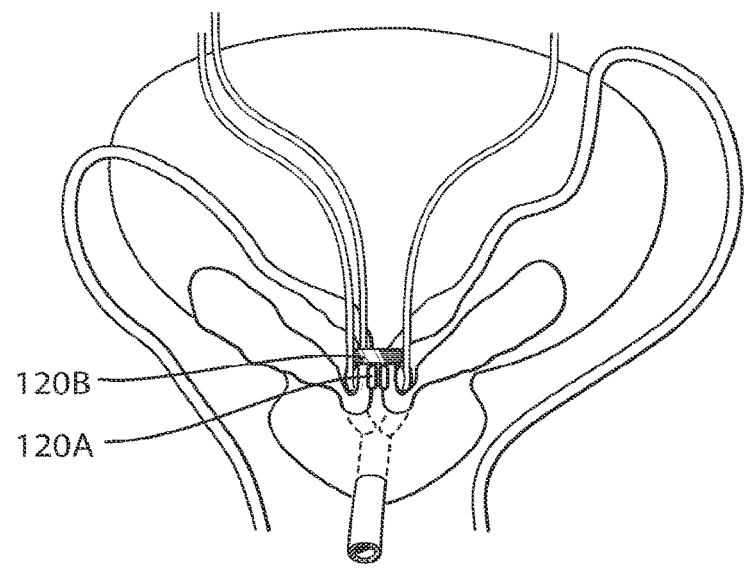
Figure 1F:
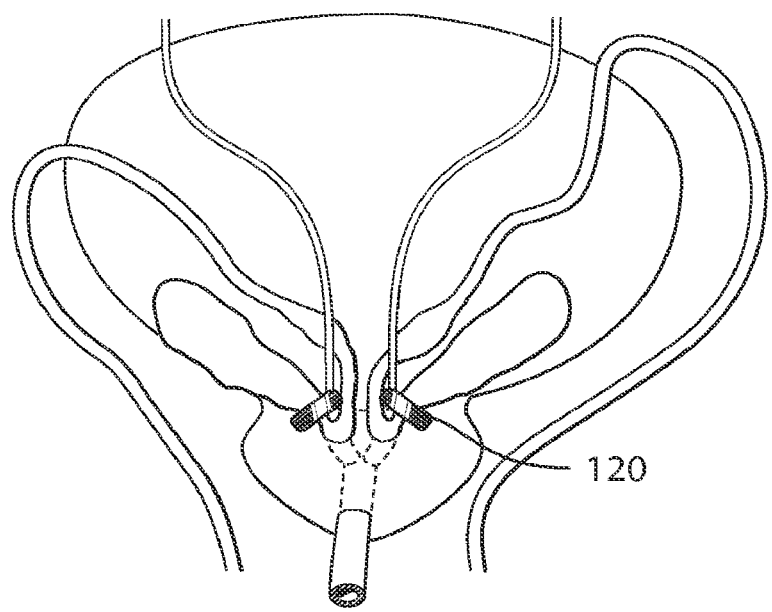

FIG. 1A is a schematic view of an apparatus for male contraception as illustrated in FIG. 1B. The apparatus 100 of FIG. 1B shows restriction of vas deferens 200A, 200B (vasa deferentia) downstream the ampulla of vas deferens 220A, 220B. The apparatus thereby is operable to temporarily prevent from reaching urethra and provide time-limited sterility. The apparatus 100 has a restriction device 120 adapted to constrict vas deferens mechanically or hydraulically and a control device 150 for controlling the operation of the restriction device as it is operated with a schematically illustrated operation device 170. The control device 150 is subcutaneously located and includes an external part and an internal part. An energizer unit (energy transmission device) 180 is capable to supply the device with wireless transmitted energy to an energy transforming device 151 connected to an energy source 152 for supplying energy consuming parts of the apparatus with energy. An external remote control unit 190 is capable of communicating with the control device 150 internal control unit 153 of the control device. The external part 150A of the control device 150 includes functions needed for external operation such as an injection port for supply of hydraulic fluid when the constriction is hydraulically operated and an activation/deactivation button for operating the restriction device. The internal part of the control device 150B can include a number of functions needed to control and operate the restriction device 120. In a hydraulically operated restriction device 120 the control device 150 can include a pump 154 operable on a reservoir for hydraulic fluid (not shown), whereby transportation of fluid from the reservoir activates the restriction device to restrict vas deferens and transportation back to the reservoir deactivates the restriction device to release vas deferens. FIG. 1C(a) shows the apparatus of FIG. 1B without any control device. The restriction device 120 is of the same type as in FIG. 1B, but it is here adapted to restrict both vas deference and the outlet ducts of the seminal vesicles. FIGS. 1C(b) and 1C(c) show the restriction device 120 schematically in an open and a closed position, respectively. FIG. 1D(a) shows an apparatus of FIG. 1B or 1C(a) with a modified restriction device 120A operating with a stimulation device on both vas deferens. The stimulation device is here represented a by set of electrodes. FIG. 1D(b) and FIG. 1D(c) show the stimulation device 120A schematically in an open and closed position, respectively. FIG. 1E shows an apparatus of FIG. 1B or 1C(a) with a restriction device comprising a stimulation device 120A and a constriction device 120B controlled by the control device to restrict both vas derence by their combined actions. In One embodiment the constriction device 120B is manually operated with a pump that operates on a reservoir to perform a constriction on vas deferens while the stimulation device operated by the control device stimulates vas deference to obtaining the sperm transport blocking effect. FIG. 1F shows another variant of the apparatus of FIG. 1B, wherein the restriction device 120 includes two constriction devices each adapted to constrict a vas deference and an outlet duct of a seminal vesicle, respectively in order to both stop the flow of sperms and seminal fluid. The function of the control device and other parts of the invention are further explained together with the FIGS. 1G to 27C, below.

FIG. 1G illustrates a system for treating a disease comprising an apparatus 10 of the present invention placed in the abdomen of a patient. An implanted energy-transforming device 302 is adapted to supply energy consuming components of the apparatus with energy via a power supply line 303. An external energy-transmission device 304 for non-invasively energizing the apparatus 10 transmits energy by at least one wireless energy signal. The implanted energy-transforming device 302 transforms energy from the wireless energy signal into electric energy which is supplied via the power supply line 303.

The wireless energy signal may include a wave signal selected from the following: a sound wave signal, an ultra-sound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 10 is operable in response to the energy of the second form. The energy-transforming device 302 may directly power the apparatus with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus, as the wireless energy is being transmitted by the energy-transmission device 304. Where the system comprises an operation device for operating the apparatus, as will be described below, the wireless energy transmitted by the energy-transmission device 304 may be used to directly power the operation device to create kinetic energy for the operation of the apparatus.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 304 also includes a wireless remote control having an external signal transmitter for transmitting a wireless control signal for non-invasively controlling the apparatus. The control signal is received by an implanted signal receiver which may be incorporated in the implanted energy-transforming device 302 or be separate there from. In this drawing and general in the coming drawings number 300 defined as a system.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 2 illustrates the system of FIG. 1G in the form of a more generalized block diagram showing the apparatus 10, the energy-transforming device 302 powering the apparatus 10 via power supply line 303, and the external energy-transmission device 304, The patient's skin 305, generally shown by a vertical line, separates the interior of the patient to the right of the line from the exterior to the left of the line.

FIG. 3 shows an embodiment of the invention identical to that of FIG. 2, except that a reversing device in the form of an electric switch 306 operable for example by polarized energy also is implanted in the patient for reversing the apparatus 10. When the switch is operated by polarized energy the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302 the electric switch 306 reverses the function performed by the apparatus 10.

FIG. 4 shows an embodiment of the invention identical to that of FIG. 2, except that an operation device 307 implanted in the patient for operating the apparatus 10 is provided between the implanted energy-transforming device 302 and the apparatus 10. This operation device can be in the form of a motor 307, such as an electric servomotor. The motor 307 is powered with energy from the implanted energy-transforming device 302, as the remote control of the external energy-transmission device 304 transmits a wireless signal to the receiver of the implanted energy-transforming device 302.

FIG. 5 shows an embodiment of the invention identical to that of FIG. 2, except that it also comprises an operation device is in the form of an assembly 308 including a motor/pump unit 309 and a fluid reservoir 310 is implanted in the patient. In this case the apparatus 10 is hydraulically operated, i.e. hydraulic fluid is pumped by the motor/pump unit 309 from the fluid reservoir 310 through a conduit 311 to the apparatus 10 to operate the apparatus, and hydraulic fluid is pumped by the motor/pump unit 309 back from the apparatus 10 to the fluid reservoir 310 to return the apparatus to a starting position. The implanted energy-transforming device 302 transforms wireless energy into a current, for example a polarized current, for powering the motor/pump unit 309 via an electric power supply line 312.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 302 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 6:
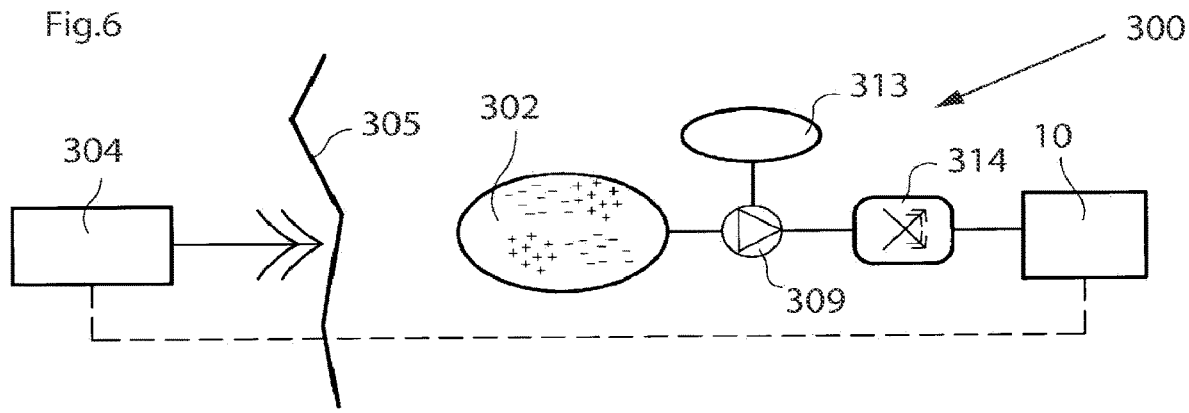

FIG. 6 shows an embodiment of the invention comprising the external energy-transmission device 304 with its wireless remote control, the apparatus 10, in this case hydraulically operated, and the implanted energy-transforming device 302, and further comprising a hydraulic fluid reservoir 313, a motor/pump unit 309 and a reversing device in the form of a hydraulic valve shifting device 314, all implanted in the patient. Of course the hydraulic operation, could easily be performed by just changing the pumping direction and the hydraulic valve may therefore be omitted. The remote control may be a device separated from the external energy-transmission device or included in the same. The motor of the motor/pump unit 309 is an electric motor. In response to a control signal from the wireless remote control of the external energy-transmission device 304, the implanted energy-transforming device 302 powers the motor/pump unit 309 with energy from the energy carried by the control signal, whereby the motor/pump unit 309 distributes hydraulic fluid between the hydraulic fluid reservoir 313 and the apparatus 10. The remote control of the external energy-transmission device 304 controls the hydraulic valve shifting device 314 to shift the hydraulic fluid flow direction between one direction in which the fluid is pumped by the motor/pump unit 309 from the hydraulic fluid reservoir 313 to the apparatus 10 to operate the apparatus, and another opposite direction in which the fluid is pumped by the motor/pump unit 309 back from the apparatus 10 to the hydraulic fluid reservoir 313 to return the apparatus to a starting position.

Figure 7:
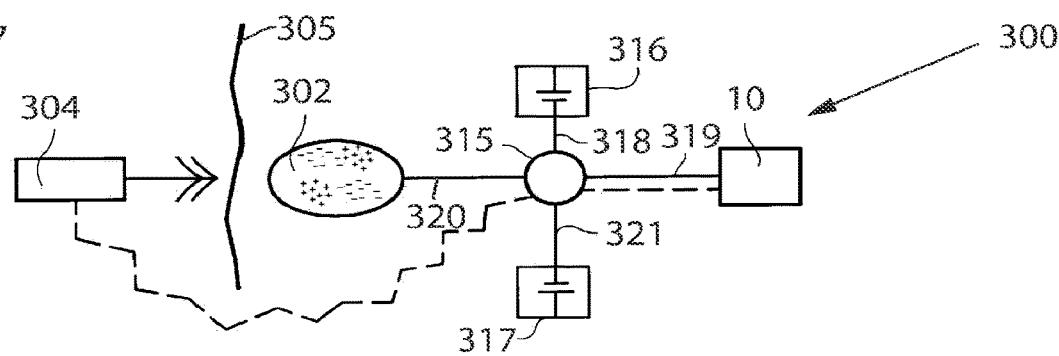

FIG. 7 shows an embodiment of the invention comprising the external energy-transmission device 304 with its wireless remote control, the apparatus 10, the implanted energy-transforming device 302, an implanted internal control unit 315 controlled by the wireless remote control of the external energy-transmission device 304, an implanted accumulator 316 and an implanted capacitor 317. The internal control unit 315 arranges storage of electric energy received from the implanted energy-transforming device 302 in the accumulator 316, which supplies energy to the apparatus 10. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 317 in the embodiment of FIG. 7-10 may be omitted. In accordance with another alternative, the accumulator 316 in this embodiment may be omitted.

Figure 8:
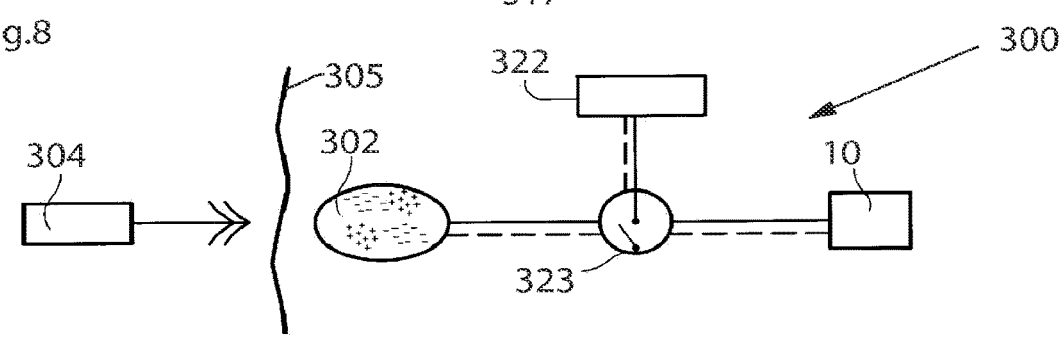

FIG. 8 shows an embodiment of the invention identical to that of FIG. 2, except that a battery 322 for supplying energy for the operation of the apparatus 10 and an electric switch 323 for switching the operation of the apparatus 10 also are implanted in the patient. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of the apparatus 10.

Figure 9:
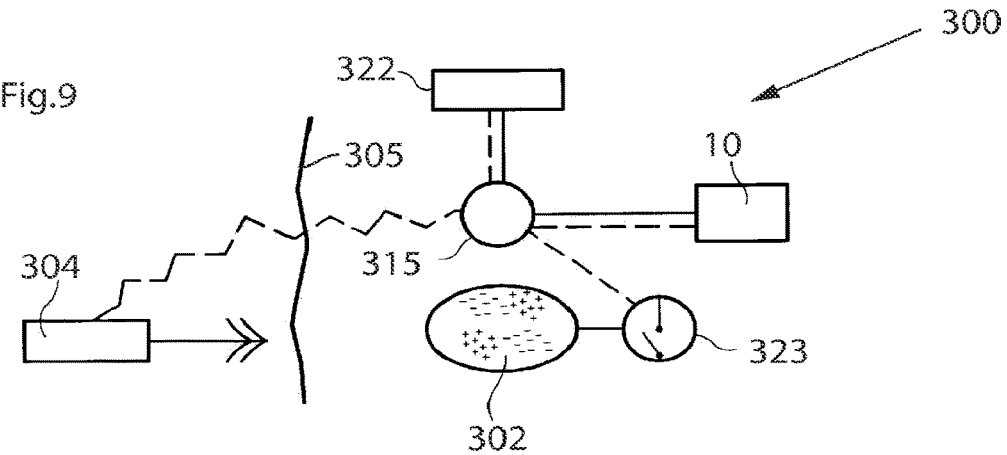

FIG. 9 shows an embodiment of the invention identical to that of FIG. 8, except that an internal control unit 315 controllable by the wireless remote control of the external energy-transmission device 304 also is implanted in the patient. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the apparatus 10.

Figure 10:
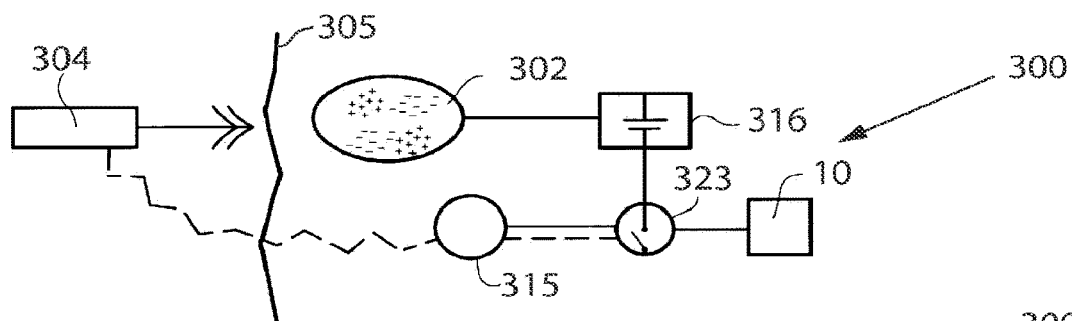

FIG. 10 shows an embodiment of the invention identical to that of FIG. 9, except that an accumulator 316 is substituted for the battery 322 and the implanted components are interconnected differently. In this case the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the apparatus 10. The accumulator may be combined with or replaced by a capacitor.

Figure 11:
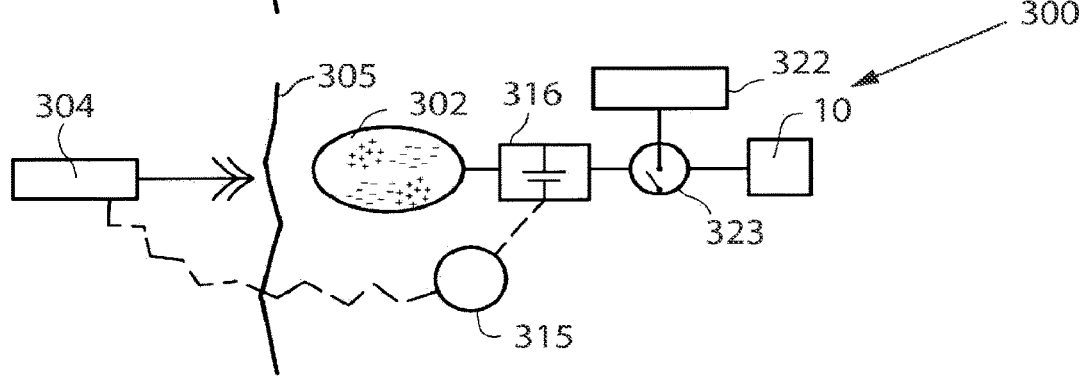

FIG. 11 shows an embodiment of the invention identical to that of FIG. 10, except that a battery 322 also is implanted in the patient and the implanted components are interconnected differently. In response to a control signal from the wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the apparatus 10.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the apparatus 10.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 12:
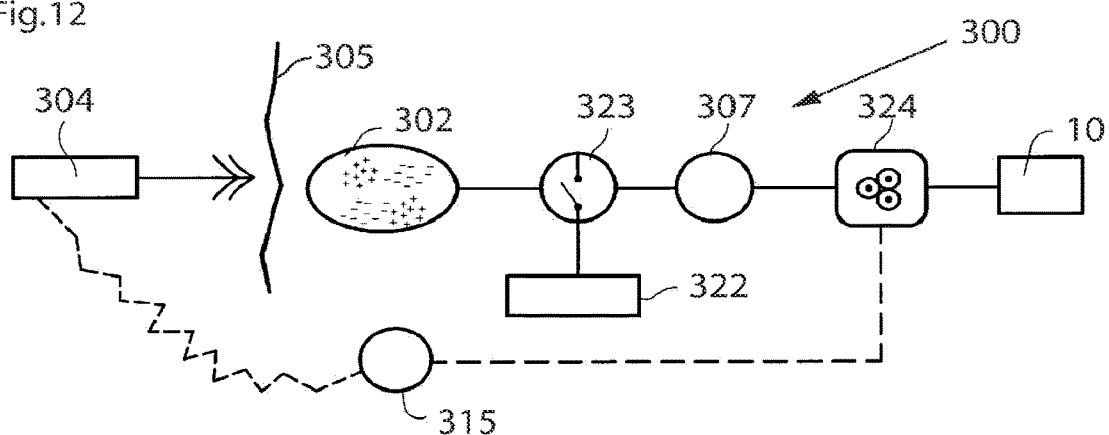

FIG. 12 shows an embodiment of the invention identical to that of FIG. 8, except that a motor 307, a mechanical reversing device in the form of a gear box 324, and an internal control unit 315 for controlling the gear box 324 also are implanted in the patient. The internal control unit 315 controls the gear box 324 to reverse the function performed by the apparatus 10 (mechanically operated). Even simpler is to switch the direction of the motor electronically. The gear box interpreted in its broadest embodiment may stand for a servo arrangement saving force for the operation device in favor of longer stroke to act.

Figure 13:
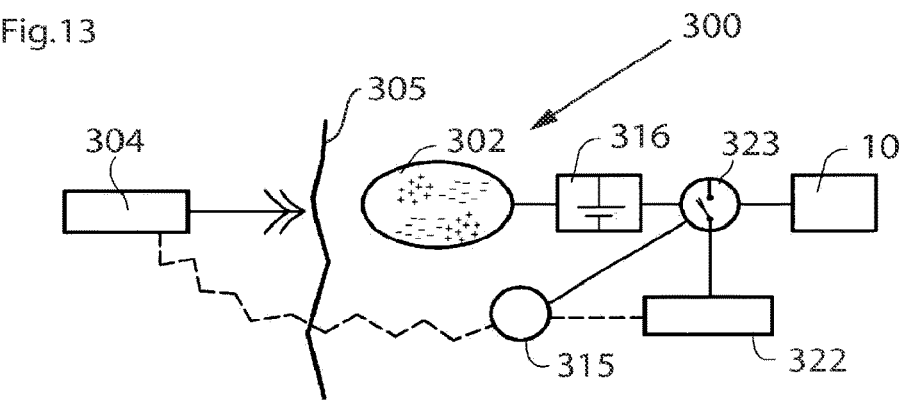
Figure 19:
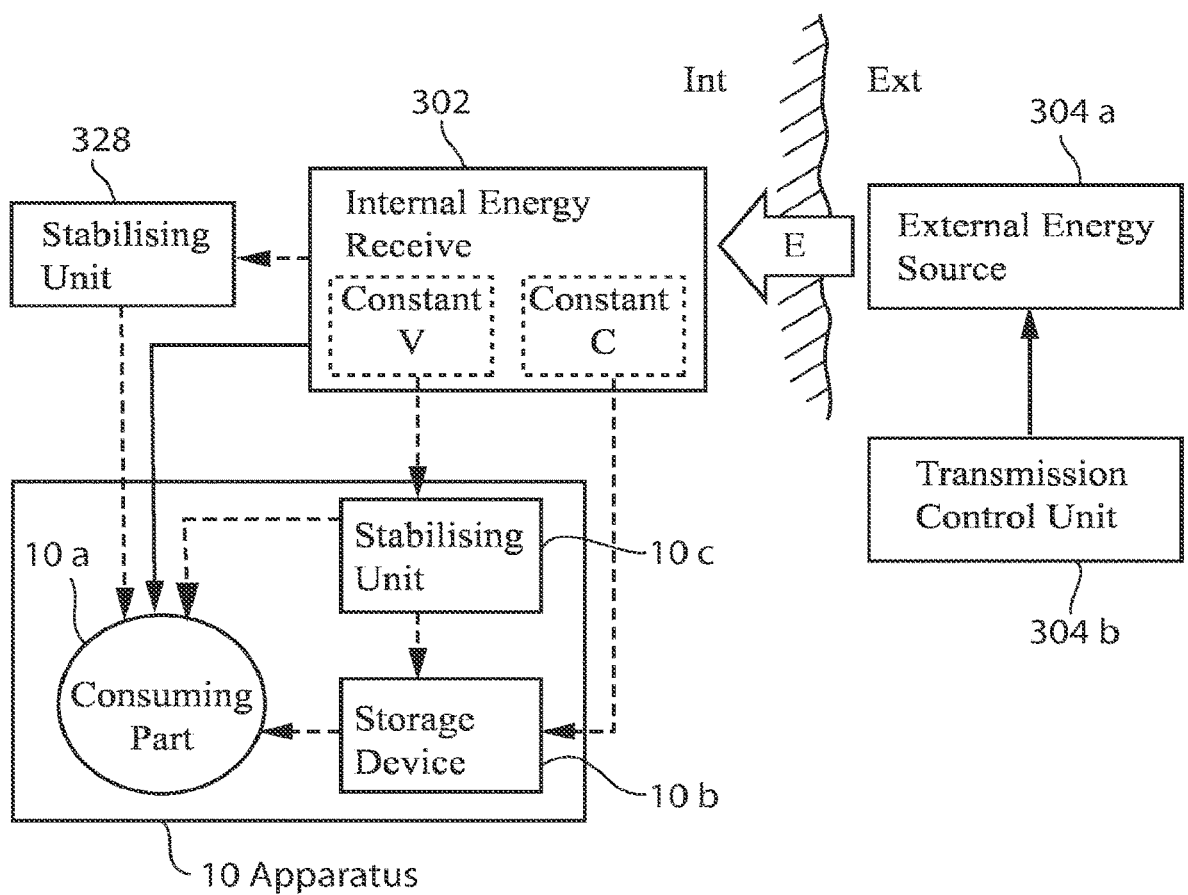
FIG. 19 is a more detailed block diagram of an arrangement for controlling the transmission of wireless energy used for the operation of the apparatus shown in FIG. 2.

FIG. 13 shows an embodiment of the invention identical to that of FIG. 19 except that the implanted components are interconnected differently. Thus, in this case the internal control unit 315 is powered by the battery 322 when the accumulator 316, suitably a capacitor, activates the electric switch 323 to switch to an on mode. When the electric switch 323 is in its on mode the internal control unit 315 is permitted to control the battery 322 to supply, or not supply, energy for the operation of the apparatus 10.

Figure 14:
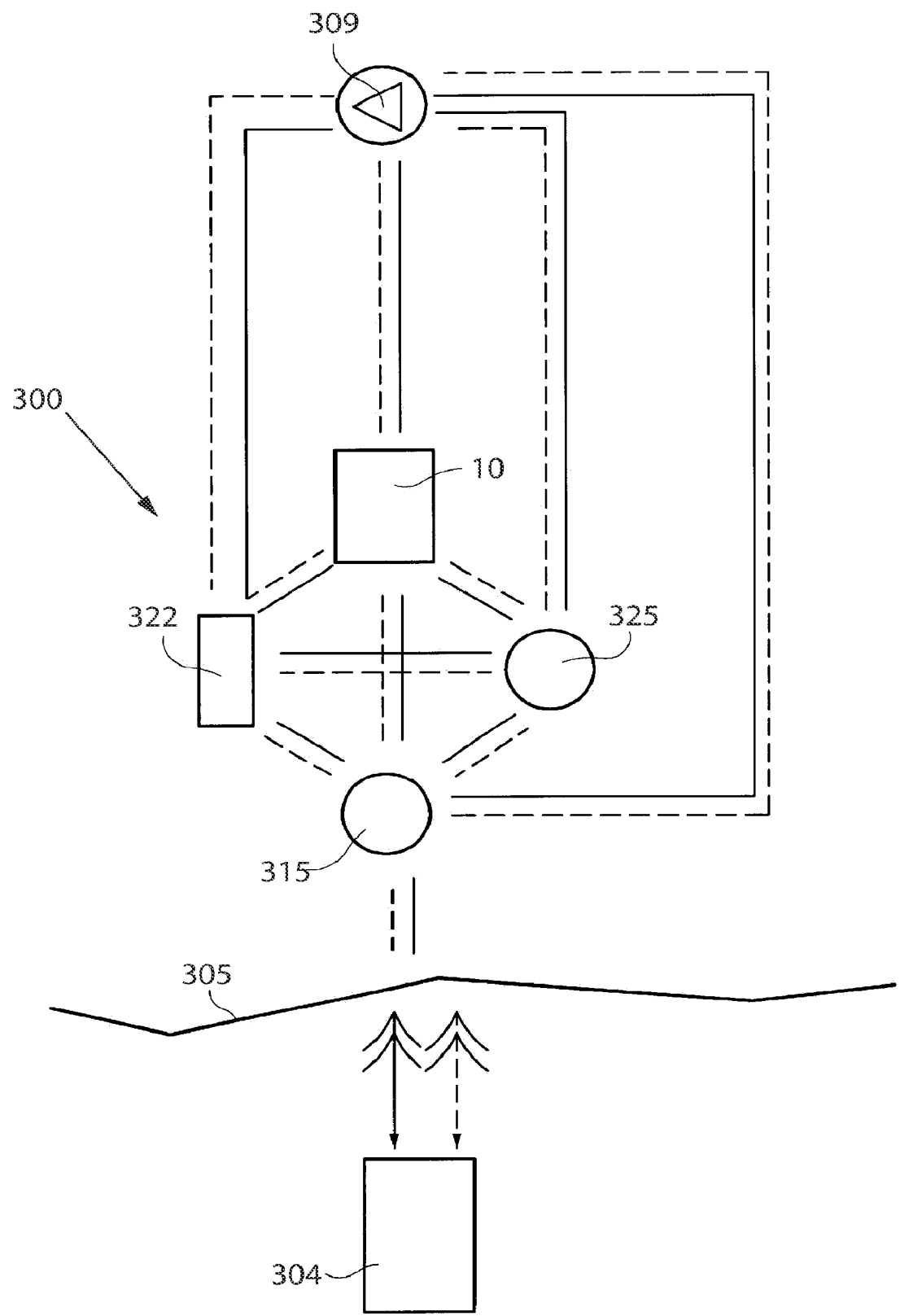

FIG. 14 schematically shows conceivable combinations of implanted components of the apparatus for achieving various communication options. Basically, there are the apparatus 10, the internal control unit 315, motor or pump unit 309, and the external energy-transmission device 304 including the external wireless remote control. As already described above the wireless remote control transmits a control signal which is received by the internal control unit 315, which in turn controls the various implanted components of the apparatus.

A feedback device, preferably comprising a sensor or measuring device 325, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 325 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 315, or alternatively the external wireless remote control of the external energy-transmission device 304, may control the apparatus 10 in response to signals from the sensor 325. A transceiver may be combined with the sensor 325 for sending information on the sensed physical parameter to the external wireless remote control. The wireless remote control may comprise a signal transmitter or transceiver and the internal control unit 315 may comprise a signal receiver or transceiver. Alternatively, the wireless remote control may comprise a signal receiver or transceiver and the internal control unit 315 may comprise a signal transmitter or transceiver. The above transceivers, transmitters and receivers may be used for sending information or data related to the apparatus 10 from inside the patient's body to the outside thereof.

Where the motor/pump unit 309 and battery 322 for powering the motor/pump unit 309 are implanted, information related to the charging of the battery 322 may be fed back. To be more precise, when charging a battery or accumulator with energy feed back information related to said charging process is sent and the energy supply is changed accordingly.

Figure 15:
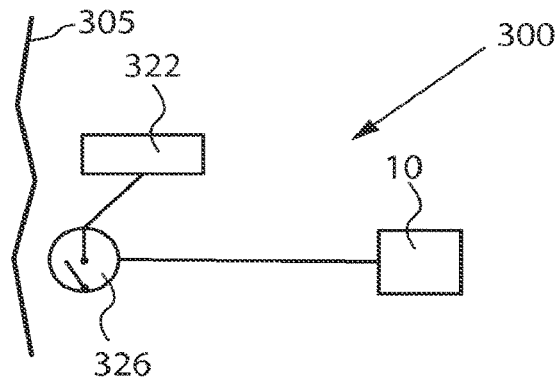

FIG. 15 shows an alternative embodiment wherein the apparatus 10 is regulated from outside the patient's body. The system 300 comprises a battery 322 connected to the apparatus 10 via a subcutaneous electric switch 326. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 16:
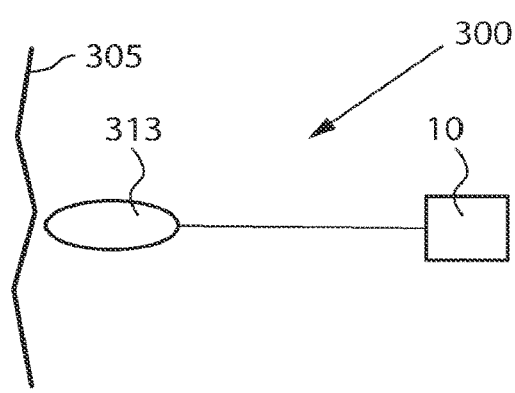

FIG. 16 shows an alternative embodiment, wherein the system 300 comprises a hydraulic fluid reservoir 313 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

Figure 17:
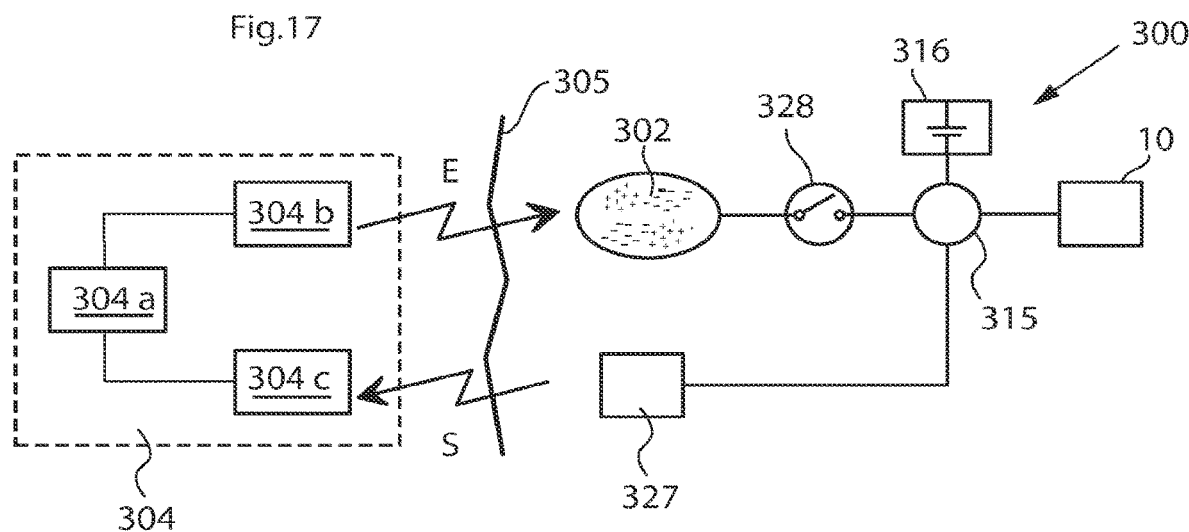
FIG. 17 is a schematic block diagram illustrating an arrangement for supplying an accurate amount of energy used for the operation of the apparatus shown in FIG. 2.

FIG. 17 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 302 connected to implanted energy consuming components of the apparatus 10. Such an energy receiver 302 may include an energy source and/or an energy-transforming device. Briefly described, wireless energy is transmitted from an external energy source 304a located outside the patient and is received by the internal energy receiver 302 located inside the patient. The internal energy receiver is adapted to directly or indirectly supply received energy to the energy consuming components of the apparatus 10 via a switch 326. An energy balance is determined between the energy received by the internal energy receiver 302 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 17 the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external energy-source 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external energy source 304a and an adjacent secondary coil arranged in the implanted energy-transforming device 302. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304b that controls the external energy source 304a based on the determined energy balance to regulate the amount of transferred energy. In order to transfer the correct amount of energy, the energy balance and the required amount of energy is determined by means of a determination device including an implanted internal control unit 315 connected between the switch 326 and the apparatus 10. The internal control unit 315 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 316 may optionally be connected to the implanted energy-transforming device 302 via the control unit 315 for accumulating received energy for later use by the apparatus 10. Alternatively or additionally, characteristics of such an accumulator, also reflecting the required amount of energy, may be measured as well. The accumulator may be replaced by a rechargeable battery and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external energy source 304a may then be regulated in response to the received control signal.

Alternatively, the determination device may include the external control unit 304b. In this alternative, sensor measurements can be transmitted directly to the external control unit 304b wherein the energy balance and/or the currently required amount of energy can be determined by the external control unit 304b, thus integrating the above-described function of the internal control unit 315 in the external control unit 304b. In that case, the internal control unit 315 can be omitted and the sensor measurements are supplied directly to the internal signal transmitter 327 which sends the measurements over to the external signal receiver 304c and the external control unit 304b. The energy balance and the currently required amount of energy can then be determined by the external control unit 304b based on those sensor measurements.

Hence, the present solution according to the arrangement of FIG. 17 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304c may be implemented as separate units using suitable signal transfer means, such as radio, IR (Infrared) or ultrasonic signals. Alternatively, the internal signal transmitter 327 and the external signal receiver 304c may be integrated in the implanted energy-transforming device 302 and the external energy source 304a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy, which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 17 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external energy source 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 18:
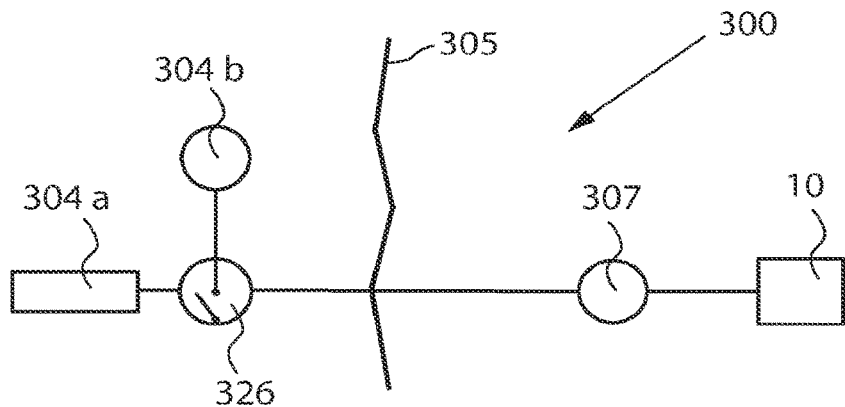
FIG. 18 schematically shows an embodiment of the system, in which the apparatus is operated with wire bound energy.

With reference to FIG. 18, although wireless transfer of energy for operating the apparatus has been described above to enable non-invasive operation, it will be appreciated that the apparatus can be operated with wire bound energy as well. Such an example is shown in FIG. 18, wherein an external switch 326 is interconnected between the external energy source 304a and an operation device, such as an electric motor 307 operating the apparatus 10. An external control unit 304b controls the operation of the external switch 326 to effect proper operation of the apparatus 10.

FIG. 19 illustrates different embodiments for how received energy can be supplied to and used by the apparatus 10. Similar to the example of FIG. 17, an internal energy receiver 302 receives wireless energy E from an external energy source 304a which is controlled by a transmission control unit 304b. The internal energy receiver 302 may comprise a constant voltage circuit, indicated as a dashed box "constant V" in the figure, for supplying energy at constant voltage to the apparatus 10. The internal energy receiver 302 may further comprise a constant current circuit, indicated as a dashed box "constant C" in the figure, for supplying energy at constant current to the apparatus 10.

The apparatus 10 comprises an energy consuming part 10a, which may be a motor, pump, restriction device, or any other medical appliance that requires energy for its electrical operation. The apparatus 10 may further comprise an energy storage device 10b for storing energy supplied from the internal energy receiver 302. Thus, the supplied energy may be directly consumed by the energy consuming part 10a, or stored by the energy storage device or the supplied energy may be partly consumed and partly stored. The apparatus 10 may further comprise an energy stabilizing unit 10c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the apparatus 10, before being consumed and/or stored by the apparatus 10. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 17 and FIG. 19 illustrate some possible but non-limiting implementation options regarding how the various shown functional components and elements can be arranged and connected to each other. However, the skilled person will readily appreciate that many variations and modifications can be made within the scope of the present invention.

Figure 20:
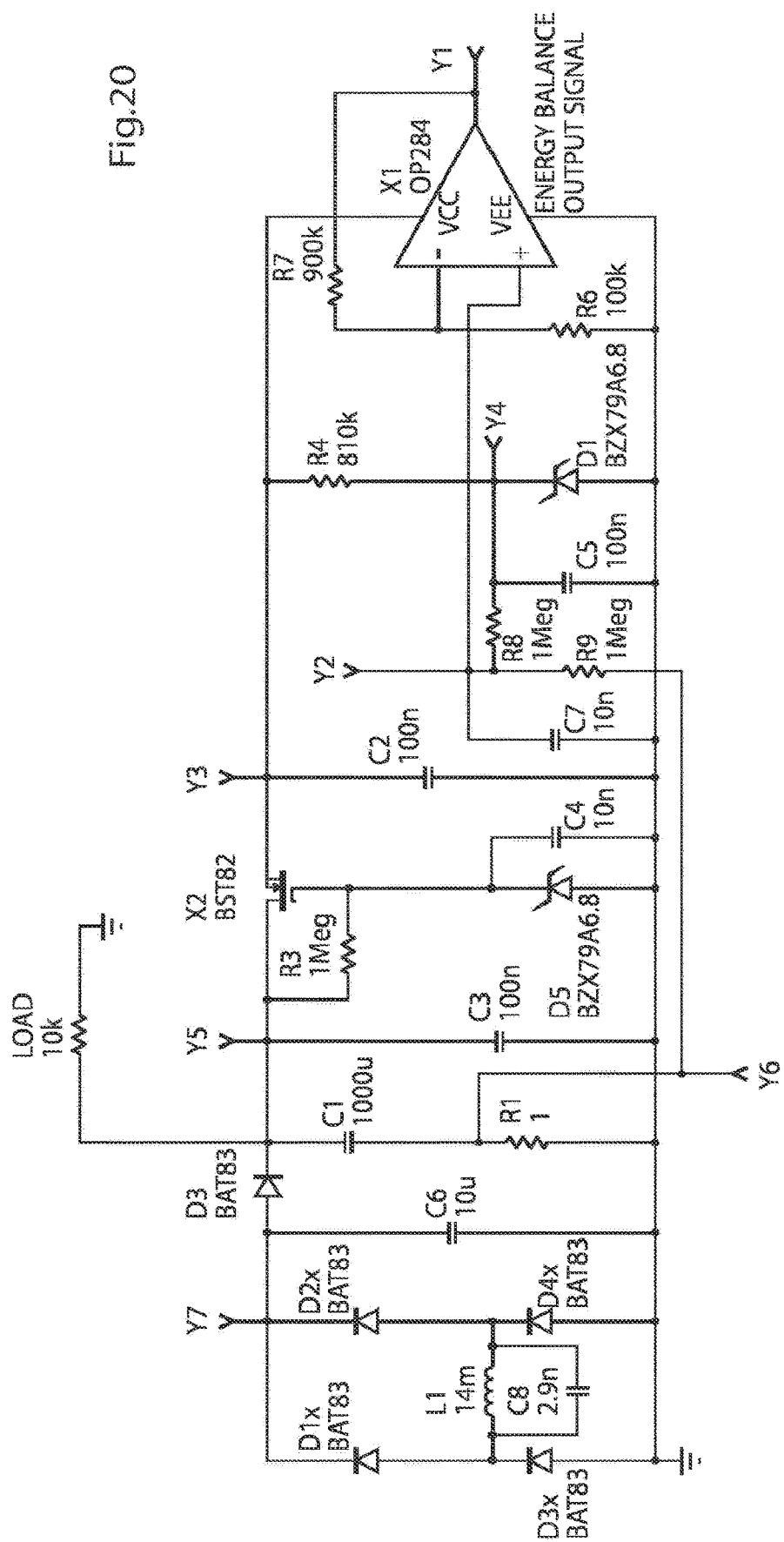
FIG. 20 is a circuit for the arrangement shown in FIG. 19, according to a possible implementation example.

FIG. 20 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 20 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 3; the transmitting parts of the system are excluded.

The implementation of the general concept of energy balance and the way the information is transmitted to the external energy transmitter can of course be implemented in numerous different ways. The schematic FIG. 20 and the above described method of evaluating and transmitting the information should only be regarded as examples of how to implement the control system.

Circuit Details

In FIG. 20 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 306 of FIG. 3 could be incorporated in any of the embodiments of FIGS. 6-12, the hydraulic valve shifting device 314 of FIG. 6 could be incorporated in the embodiment of FIG. 5, and the gear box 324 could be incorporated in the embodiment of FIG. 4. Please observe that the switch simply could mean any electronic circuit or component.

The embodiments described in connection with FIGS. 17, 19 and 20 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 21-24 show in more detail block diagrams of four different ways of hydraulically or pneumatically powering an implanted apparatus according to the invention.

Figure 21:
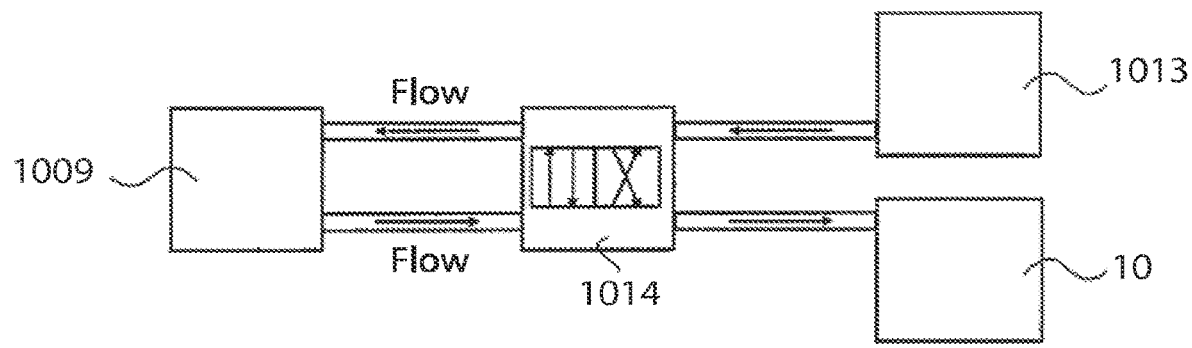
FIGS. 21-27 show various ways of arranging hydraulic or pneumatic powering of an apparatus implanted in a patient.

FIG. 21 shows a system as described above with. The system comprises an implanted apparatus 10 and further a separate regulation reservoir 1013, a one way pump 1009 and an alternate valve 1014.

Figure 22:
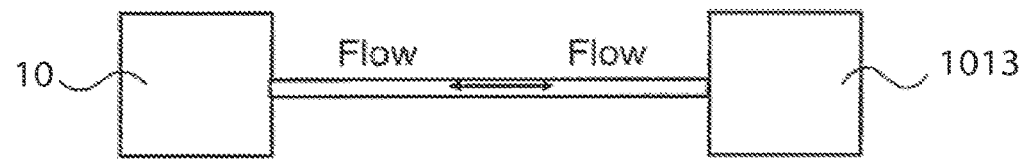

FIG. 22 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 23:
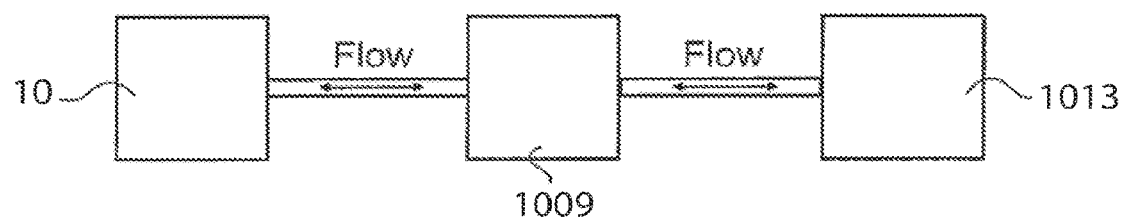

FIG. 23 shows the apparatus 10, a two way pump 1009 and the regulation reservoir 1013.

Figure 24:
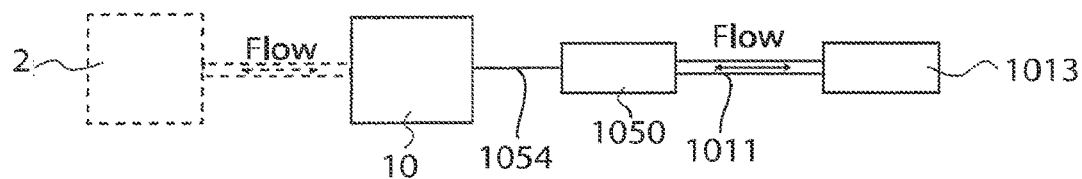
Figure 25:
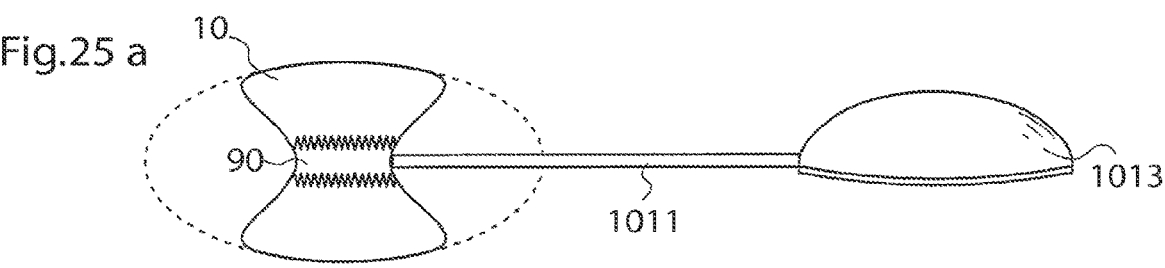
Figure 25:
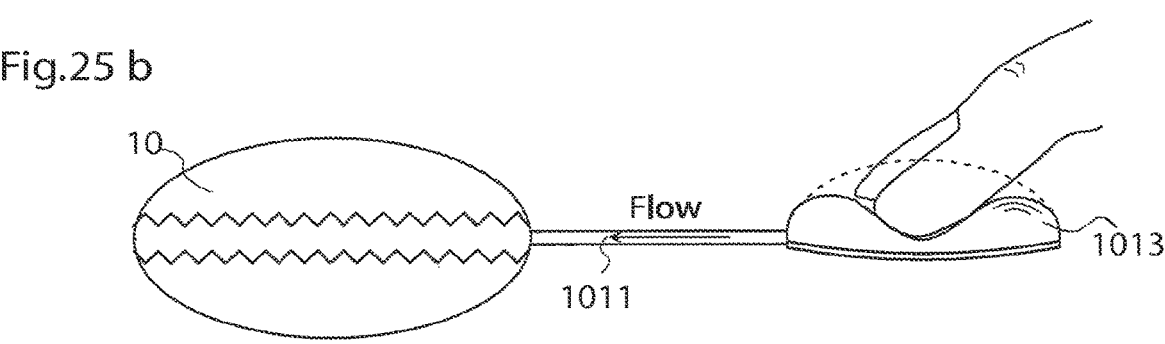
Figure 25:
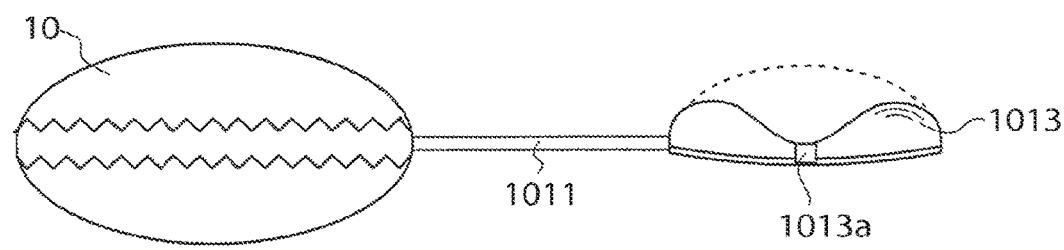
Figure 26:
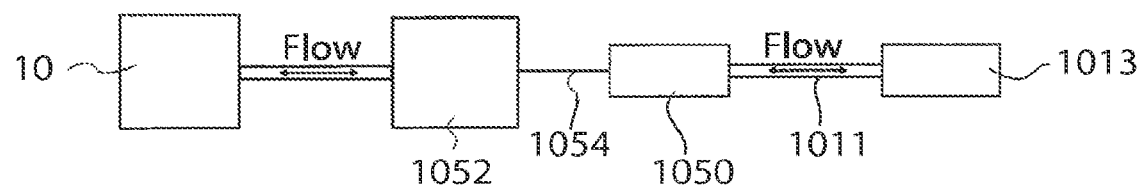
Figure 27:
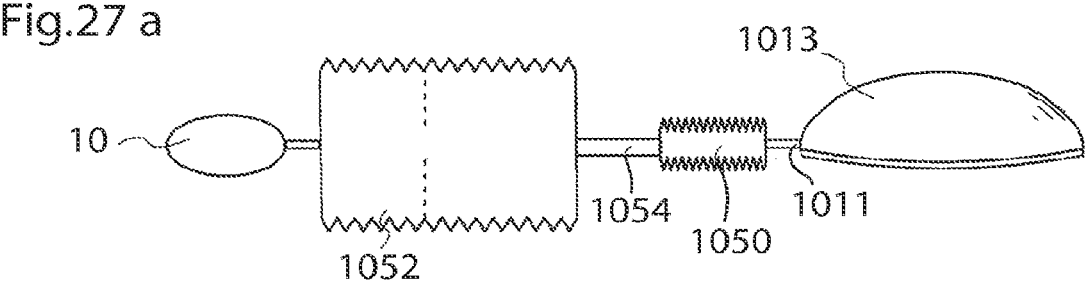
Figure 27:
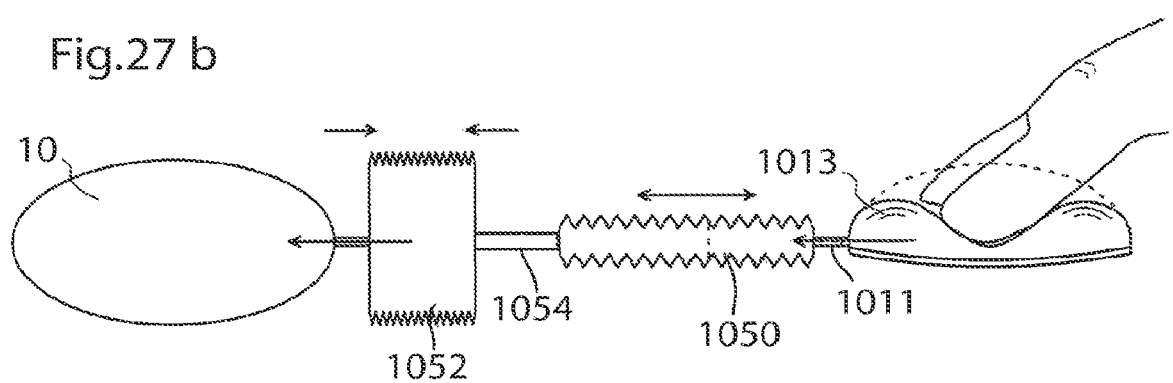
Figure 27:
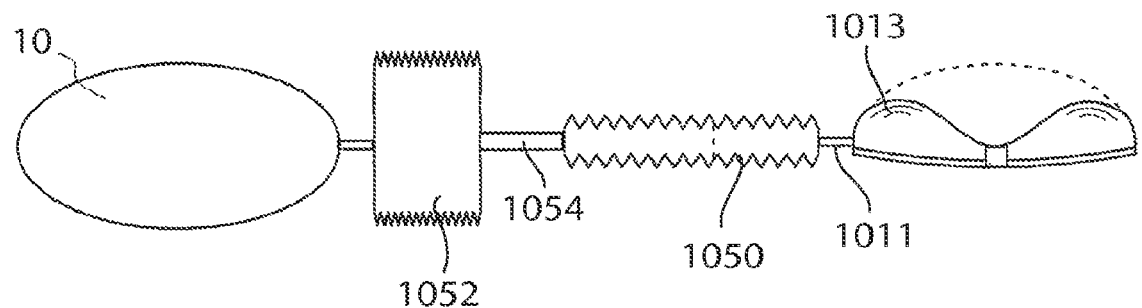

FIG. 24 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contractable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050.

The servo reservoir 1050 can also be part of the apparatus itself.

In one embodiment, the regulation reservoir is placed subcutaneous under the patient's skin and is operated by pushing the outer surface thereof by means of a finger. This system is illustrated in FIGS. 25a-c. In FIG. 25a, a flexible subcutaneous regulation reservoir 1013 is shown connected to a bulge shaped servo reservoir 90 by means of a conduit 1011. This bellow shaped servo reservoir 90 is comprised in a flexible apparatus 10. In the state shown in FIG. 25a, the servo reservoir 90 contains a minimum of fluid and most fluid is found in the regulation reservoir 1013. Due to the mechanical interconnection between the servo reservoir 90 and the apparatus 10, the outer shape of the apparatus 10 is contracted, i.e., it occupies less than its maximum volume. This maximum volume is shown with dashed lines in the figure.

FIG. 25b shows a state wherein a user, such as the patient in with the apparatus is implanted, presses the regulation reservoir 1013 so that fluid contained therein is brought to flow through the conduit 1011 and into the servo reservoir 90, which, thanks to its bellow shape, expands longitudinally. This expansion in turn expands the apparatus 10 so that it occupies its maximum volume, thereby constricting vas deferens downstream the ampulla (not shown), which it contacts.

The regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 26 and 27*a-c*. The block diagram shown in FIG. 26 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contractable cavity is in turn controlled by the larger adjustable reservoir 1052 by supply of hydraulic fluid from the larger adjustable reservoir 1052 in fluid connection with the apparatus 10.

An example of this embodiment will now be described with reference to FIG. 27*a-c*. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 31*a*, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 25*a-c*, the regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

The invention claimed is:

1. A male contraception apparatus for obtaining temporary sterility during intercourse of a male human being, the male human being having respective left and right vas deferens connecting between respective left and right testes and an urethra, and further having respective left and right ampulla vas deferens being an enlargement of each of the left and right vas deferens positioned close to a prostate gland and seminal vesicle ducts, the ampulla vas deferens acting as a sperm reservoir and being located close to where the vas deferens meets the seminal vesicle, the male contraception apparatus comprising:

an implantable hydraulic restriction device, configured to restrict vas deferens during a controlled temporary period using hydraulic force during sexual intercourse to hinder sperm to reach the urethra during intercourse so as to obtain the temporary sterility and, thus, configured to release the restriction of the vas deferens between intercourses, when implanted, wherein the hydraulic restriction device comprises a constriction device configured to constrict at least one portion of a tissue wall of vas deferens to stop the flow in the vas deferens, the implantable restriction device further configured to be accommodated, when implanted, in at least a region downstream the ampulla vas deferens and to restrict, when implanted in said region, at least the vas deferens in a downstream region of the ampulla vas deferens, a sensor configured to sense a temperature of the male contraception apparatus, and a control device configured to control the restriction device, when implanted in said region, to apply a pressure to said at least one portion of the tissue wall, said pressure being adapted to restrict at least the downstream region of the ampulla vas deferens during sexual intercourse to stop the flow in the vas deferens and, thus, configured to control the release of the restriction at least of the downstream region of the ampulla vas deferens in between sexual intercourses and to hinder sperm to reach the urethra for the controlled temporary period during sexual intercourse, by activation of the restriction device, wherein the control device is further configured to send feedback information pertaining to the temperature to an external device outside the male human being's body, and wherein the control device comprises at least one of:

a hydraulic reservoir, which is hydraulically connected to the apparatus, wherein the apparatus is adapted to be non-invasively regulated by manually pressing the hydraulic reservoir to operate the restriction device, a manual pump operating on the hydraulic reservoir to operate the restriction device to perform a constriction of vas deferens, a wireless receiver for receiving signals from a remote control for non-invasively controlling the apparatus, and at least one switch implantable in the patient for manually and non-invasively controlling the apparatus.

2. The apparatus according to claim 1, further comprising a hydraulic operation device for hydraulically operating the constriction device to change the constriction of a wall portion of vas deferens and wherein the constriction device is adjustable.

3. The apparatus according to claim 2 wherein the hydraulic operation device is electrically powered.

4. The apparatus according to claim 3 wherein the operation device comprises a motor.

5. The apparatus according to claim 4 wherein the operation device comprises a servo system.

6. The apparatus according to claim 1, wherein the constriction device comprises at least two elongated clamping elements extending along the organ in the direction of flow in the patient's vas deferens on different sides of the vas deferens, and the operation device operates the clamping elements to clamp the wall portion between the clamping elements to constrict the wall portion.

7. The apparatus according to claim 1, wherein the restriction device comprises a stimulation device configured to stimulate a wall portion of the tissue wall of vas deferens in the region downstream the ampulla to contract said wall portion to influence the flow in the vas deferens.

8. The apparatus according to claim 7, wherein the control device controls the stimulation device to adjust the intensity of the stimulation of the wall portion in response to the sensed temperature of the apparatus or in response to a sensed physical parameter of the patient.

9. The apparatus according to claim 7, wherein the control device controls the stimulation device in a first mode to stimulate the constricted wall portion to stop the flow in the vas deferens and controls the stimulation device in a second mode to cease the stimulation of the wall portion to allow flow in the vas deferens.

10. The apparatus according to claim 7, wherein the control device controls the stimulation device to stimulate one or more different areas of the wall portion at a time, and wherein the control device controls the stimulation device to cyclically propagate the stimulation of the areas along the wall portion in the opposite direction of the flow in the patient's vas deferens, or to propagate the stimulation of the areas in accordance with a determined stimulation pattern.

11. The apparatus according to claim 7, wherein the stimulation device is adapted to stimulate the areas of the patient's wall portion with electric pulses, wherein the stimulation device comprises at least one electrical element for engaging the wall portion and for stimulating the wall portion with electric pulses, or wherein the stimulation device comprises a plurality of electrical elements.

12. The apparatus according to claim 1, comprising an operation device, comprising a regulated hydraulic reservoir and a pump,
    wherein the restriction device is hydraulically operated, and the control device is adapted to control the pump operable on or pumping fluid between the regulated hydraulic reservoir and the restriction device for operating the apparatus,
    wherein transportation of fluid from the regulated hydraulic reservoir activates the restriction device to restrict vas deferens and transportation back to the regulated hydraulic reservoir deactivates the restriction device to release vas deferens, and
    wherein the regulated hydraulic reservoir is adapted to be regulated by moving a wall part of the regulated hydraulic reservoir, allowing free passage of fluid any time by moving the regulated hydraulic reservoir wall.

13. The apparatus according to claim 1, wherein the restriction device is adapted to restrict at least one of:
    vasa deferentia both left and right side together, and
    vasa deferentia both left and right side together as well as both outlet ducts of the seminal vesicles.

14. The apparatus according to claim 1, comprising a second restriction device, the restriction device and second restriction device is adapted to restrict on one side each, the left and right side, each restriction device adapted to restrict at least one of:
    one vas deferens, and
    one vas deferens together with the closely located outlet duct of the seminal vesicle.

15. The apparatus according to claim 1, being part of a system comprising an implantable internal energy source for powering implantable energy consuming components of the apparatus.

16. The apparatus according to claim 15, being part of a system comprising an external energy source for transferring energy in a wireless mode,
    wherein the implantable energy source is chargeable by the energy transferred in a wireless mode.

17. The apparatus according to claim 1, wherein the restriction device is configured to restrict at least two lumens, in at least one of the following alternatives: at least two vas deferens, one vas deferens and one seminal vesicle duct, and two vas deferens and two seminal vesicle ducts.

18. Method of use of a male contraception apparatus for obtaining temporary sterility during sexual intercourse of a male mammalian individual,
    wherein said male mammalian individual has respective left and right vas deferens connecting between respective left and right testes and an urethra, and further has respective left and right ampulla vas deferens being an enlargement of each of the left and right vas deferens close to a prostate gland and seminal vesicle ducts, the ampulla vas deferens acting as a sperm reservoir and being located close to where the vas deferens meets the seminal vesicle, and
    wherein the male contraception apparatus comprises an implantable hydraulic restriction device configured to restrict vas deferens during a controlled temporary period during sexual intercourse to hinder sperm to reach the urethra during intercourse so as to obtain the temporary sterility and, thus, configured to release the restriction of the vas deferens between intercourses, when implanted, and further configured to be accommodated, when implanted, in a region at least downstream the ampulla and to restrict, when implanted in said region, the vas deferens at least in a downstream region of the ampulla vas deferens, wherein the hydraulic restriction device comprises a constriction device configured to constrict at least one portion of a tissue wall of vas deferens to stop the flow in the vas deferens,
    wherein the male contraception apparatus further comprises a sensor configured to sense a temperature of the male contraception apparatus, and
    wherein the male contraception apparatus further comprises a control device configured to control the operation of the hydraulic restriction device, when implanted in said region between the prostate gland and the ampulla vas deferens, to apply a pressure to said at least one portion of the tissue wall, said pressure being adapted to restrict at least the downstream region of the ampulla vas deferens during sexual intercourse to stop the flow in the vas deferens and, thus, configured to control the release of the restriction of at least the downstream region of the ampulla vas deferens in between sexual intercourses and to hinder sperm to reach the urethra for the controlled temporary period during sexual intercourse, by activation of the hydraulic restriction device in at least the downstream region of the ampulla vas deferens, wherein the control device is further configured to send feedback information pertaining to the temperature to an external device outside the male human being's body, and wherein the control device comprises at least one of:
    a hydraulic reservoir, which is hydraulically connected to the apparatus, wherein the apparatus is adapted to be non-invasively regulated by manually pressing the hydraulic reservoir to operate the restriction device,
    a manual pump operating on the hydraulic reservoir to operate the restriction device to perform a constriction of vas deferens,
    a wireless receiver for receiving signals from a remote control for non-invasively controlling the apparatus, and
    at least one switch implantable in the patient for manually and non-invasively controlling the apparatus,
    wherein the method comprises the use of the male contraception apparatus, by the control of the control device, to restrict the vas deferens in the region downstream the ampulla vas deferens during a controlled period and, thereby, prevent sperms from the ampulla vas deferens to reach the urethra.

19. Method of implantation of a male contraception apparatus for obtaining temporary sterility during sexual intercourse of a male mammalian individual, wherein said male mammalian individual has respective left and right vas deferens connecting between respective left and right testes and an urethra, and further has respective left and right ampulla vas deferens being an enlargement of each of the left and right vas deferens close to a prostate gland and seminal vesicle ducts, the ampulla vas deferens acting as a sperm reservoir and being located close to where the vas deferens meets the seminal vesicle, and wherein the male contraception apparatus comprises an implantable hydraulic restriction device configured to restrict vas deferens during a controlled temporary period during sexual intercourse to hinder sperm to reach the urethra during intercourse so as to obtain the temporary sterility and, thus, configured to release the restriction of the vas deferens between intercourses, when implanted, and further configured to be accommodated, when implanted, in at least a region downstream the ampulla vas deferens and to restrict, when implanted in said region, the vas deferens at least in a downstream region of the ampulla vas deferens, wherein the hydraulic restriction device comprises a constriction device configured to constrict at least one portion of a tissue wall of vas deferens to stop the flow in the vas deferens, wherein the male contraception apparatus further comprises a sensor configured to sense a temperature of the male contraception apparatus, and wherein the male contraception apparatus further comprises a control device configured to control the operation of the hydraulic restriction device, when implanted in said region, to apply a pressure to said at least one portion of the tissue wall, said pressure being adapted to restrict at least the downstream region of the ampulla vas deferens during sexual intercourse to stop the flow in the vas deferens and, thus, configured to control the release of the restriction of at least the downstream region of the ampulla vas deferens in between sexual intercourses and to hinder sperm to reach the urethra for the controlled temporary period during sexual intercourse, by activation of the hydraulic restriction device in at least the downstream region of the ampulla vas deferens, wherein the control device is further configured to send feedback information pertaining to the temperature parameter to an external device outside the male human being's body, and wherein the control device comprises at least one of:

a hydraulic reservoir, which is hydraulically connected to the apparatus, wherein the apparatus is adapted to be non-invasively regulated by manually pressing the hydraulic reservoir to operate the restriction device, a manual pump operating on the hydraulic reservoir to operate the restriction device to perform a constriction of vas deferens, a wireless receiver for receiving signals from a remote control for non-invasively controlling the apparatus, and at least one switch implantable in the patient for manually and non-invasively controlling the apparatus, wherein the method comprises the step of implanting the male contraception apparatus in said region at least downstream the ampulla vas deferens so as to allow use of the male contraception apparatus to restrict the vas deferens during a controlled period and, thereby, prevent sperms from the ampulla vas deferens to reach the urethra.

20. The method according to claim 19, further comprising implanting an implantable internal energy source for powering implantable energy consuming components of the apparatus.

21. The method according to claim 19, further comprising implanting an implantable energy receiver for receiving energy in a wireless mode.

22. The method according to claim 19, further comprising implanting an operation device, comprising at least one of: a motor, a pump, and a motor and a pump.

23. The method according to claim 19, further comprising implanting a servo system.

24. The method according to claim 19, wherein the constriction device comprises at least two elongated clamping elements and wherein the method comprises implanting the at least two elongated clamping elements such that they extend along the vas deferens in the direction of flow in the patient's vas deferens on different sides of the vas deferens.

* * * * *